United States Patent [19]
Regnery et al.

[11] Patent Number: 5,958,414
[45] Date of Patent: Sep. 28, 1999

[54] COMPOSITION TO PROTECT A MAMMAL AGAINST *BARTONELLA HENSELAE* INFECTION

[75] Inventors: Russell L. Regnery, Tucker; Jane A. Rooney, Decatur, both of Ga.; Sharon A. Jenkins, Peabody, Mass.

[73] Assignees: Heska Corporation, Fort Collins, Colo.; Avant Immunotherapeutics, Inc., Needham, Mass.; The United States of America as represented by the Department of Health and Human Services, Washington, D.C.

[21] Appl. No.: 08/922,970

[22] Filed: Sep. 3, 1997

[51] Int. Cl.$^6$ .......................... A61K 39/00; A61K 45/00; A61K 39/002; C12N 1/00
[52] U.S. Cl. ..................... 424/184.1; 424/278.1; 424/280.1; 424/269.1; 435/243
[58] Field of Search ................ 424/184.1, 278.1, 424/280.1, 269.1; 435/263

[56] References Cited

U.S. PATENT DOCUMENTS

| | | | |
|---|---|---|---|
| 4,880,622 | 11/1989 | Allcock et al. | 424/78 |
| 5,399,485 | 3/1995 | Regnery et al. | 435/7.32 |
| 5,494,673 | 2/1996 | Andrianov et al. | 424/280.1 |
| 5,500,161 | 3/1996 | Andrianov et al. | 264/8 |
| 5,529,777 | 6/1996 | Andrianov et al. | 424/184.1 |
| 5,644,047 | 7/1997 | Anderson et al. | 536/23.7 |
| 5,693,776 | 12/1997 | Anderson et al. | 536/23.1 |
| 5,736,347 | 4/1998 | Anderson et al. | 435/7.32 |

OTHER PUBLICATIONS

Burgess et al., 1998, *Microbial Pathogenesis*, vol. 25, pp. 157–164.

Dehio et al., 1997, *Journal of Cell Science*, vol. 110, pp. 2141–2154.

Mehock et al., 1998, *Infection and Immunity*, vol. 66(7), pp. 3462–3466.

Regnath et al., 1998, *Infection and Immunity*, vol. 66(11), pp. 5534–5536.

RL Regnery et al. Clin. Infect. Dis. 21 (Suppl.): S94–S98, 1995.

Allcock et al., 1989, "An Ionically Cross–Linkable Polyphosphazene: Poly[bis(carboxylatophenoxy)phosphazene] and Its Hydrogels and Membranes," *Macromolecules*, 22, pp. 75–79.

Regnery et al., 1992, "Naturally occurring 'Rochalimaea henselae' infection in domestic cat," Letter to the Editor, *The Lancet*, vol. 340, pp. 557–558.

Regnery, et al., 1992, "Serolgical response to 'Rochalimaea henselae' antigen in suspected cat–scratch disease," *The Lancet*, vol. 339, pp. 1443–1446.

*Primary Examiner*—James C. Housel
*Assistant Examiner*—S. Devi
*Attorney, Agent, or Firm*—Heska Corporation

[57] ABSTRACT

The present invention relates to a therapeutic composition to protect a mammal from *B. henselae* infection that includes an isolated *B. henselae* antigen and an adjuvant comprising a phosphazene polymer. Also included is a method to use such a therapeutic composition to protect a mammal from *B. henselae* infection. One embodiment is a method to protect a human from cat scratch disease by administering such a therapeutic composition to a domestic cat in contact with the human. The present invention also includes a method to produce such a therapeutic composition.

36 Claims, No Drawings

COMPOSITION TO PROTECT A MAMMAL AGAINST *BARTONELLA HENSELAE* INFECTION

FIELD OF THE INVENTION

The present invention relates to a novel composition to protect a mammal from *Bartonella henselae* infection. In particular, the present invention relates to a composition comprising a *Bartonella henselae* antigen and a phosphazene polymer adjuvant.

BACKGROUND OF THE INVENTION

Cat scratch disease (CSD) has been the subject of considerable clinical and microbiological interest for many years. An estimated 24,000 cases of CSD occur each year in the United States, and CSD is responsible for up to 2,000 human hospitalizations. CSD is described as a subacute regional lymphadenitis temporally associated with the scratch or bite of a cat, which occasionally results in meningoencephalitis. Very serious sequelae of CSD have been reported in immunocompromised individuals. The inventors, however, are not aware of any reports of clinical disease in cats despite the fact that cats are the reservoir for the etiologic agent of CSD.

The etiologic agent of CSD is the bacterium *Bartonella henselae* (*B. henselae*), formerly called *Rochalimaea henselae*. See for example, Regnery, et al., 1992, "Serological response to '*Rochalimaea henselae*' antigen in suspected cat-scratch disease," *The Lancet*, Vol. 339, pp. 1443–1446; Regnery, et al., 1992, "Naturally occurring '*Rochalimaea henselae*' infection in domestic cat," *The Lancet*, Vol. 340, pp. 557–558; U.S. Pat. No. 5,399,485, by Anderson et al, issued Mar. 21, 1995 (Anderson et al, '485); and U.S. Pat. No. 5,644,047, by Anderson et al, issued Jul. 1, 1997 (Anderson et al, '047). Anderson et al, '485, ibid. and Anderson et al, '047, ibid. are each incorporated herein by reference in its entirety. Treatment with antibiotics does not appear to affect the outcome of cat scratch disease. Because cats are the reservoir for *B. henselae*, they are the source of infection in humans. As such, exposure of humans to *B. henselae* infection may best be controlled by controlling the bacterium in cats, especially pet cats that have frequent contact with humans.

Many compounds with adjuvant properties are used to enhance the immune response to antigens, but it is unpredictable as to which compound(s) will serve as a suitable adjuvant for a particular antigen. Thus, it is not clear what adjuvants would be suitable to enhance an effective immune response against *B. henselae* infection. Furthermore, although cats that are experimentally infected with *B. henselae* are resistant to subsequent infection, it is not known what type of immune response is responsible for this resistance. Thus, as far as the inventors are aware, there is no scientific information to help select an adjuvant that would work.

SUMMARY OF THE INVENTION

The present invention is based on the surprising discovery that a polyphosphazene adjuvant enhances the immune response of a *B. henselae* antigen to such an extent that a vaccine comprising a *B. henselae* antigen and polyphosphazene adjuvant provides full protection against *B. henselae* infection coupled with acceptable reactogenicity.

One embodiment of the present invention is a therapeutic composition to protect a mammal from *B. henselae* infection; the therapeutic composition includes (a) an isolated *B. henselae* antigen and (b) an adjuvant comprising a phosphazene polymer. A preferred *B. henselae* antigen includes whole inactivated *B. henselae* cells. Particularly preferred *B. henselae* antigens include iBhV-Ag, iBhA-Ag, and iBhB-Ag. A preferred phosphazene polymer is a phosphazene polyelctrolyte polymer which is at least partially soluble in water. A particularly preferred phosphazene polymer is poly[di(carboxylatophenoxy)phosphazene] (i.e., PCPP). In one embodiment the therapeutic composition also includes an excipient, a carrier, and/or an additional adjuvant.

The present invention also includes a method to protect a mammal from *B. henselae* infection, which includes the step of administering to the mammal a therapeutic composition that includes (a) an isolated *B. henselae* antigen and (b) an adjuvant comprising a phosphazene polymer. Preferred mammals to protect include felids and primates, with domestic cats and humans being particularly preferred.

Another embodiment of the present invention is a method to protect a human from cat scratch disease, caused by *B. henselae* infection, which includes the step of administering to a domestic cat in contact with the human (i.e., a cat that exists in close proximity with a human such that a *B. henselae* infected cat can infect a human) a therapeutic composition that includes (a) an isolated *B. henselae* antigen and (b) an adjuvant comprising a phosphazene polymer.

Yet another embodiment of the present invention is a method to produce a therapeutic composition to protect a mammal from *B. henselae* infection. The method includes the steps of (a) growing *B. henselae* cells, (b) preparing an isolated *B. henselae* antigen from the cells, and (c) mixing the isolated *B. henselae* antigen with an adjuvant that includes a phosphazene polymer. Preferred steps of preparing the *B. henselae* antigen include inactivation, disruption, fractionation, and attenuation. Preferred steps of mixing include combining the isolated *B. henselae* antigen with a soluble phosphazene polymer, combining the isolated *B. henselae* antigen with a polyphosphazene microparticle, and microencapsulating the isolated *B. henselae* antigen in a polyphosphazene microparticle.

DETAILED DESCRIPTION OF THE INVENTION

The present invention provides a therapeutic composition to protect an animal from *B. henselae* infection which comprises an isolated *B. henselae* antigen combined with a polyphosphazene adjuvant. It was a surprising finding that polyphosphazene adjuvants worked well in the present invention. It will be well-appreciated by those of skill in the art that selection of a suitable adjuvant (described herein) is a critical, but unpredictable facet of the art. As disclosed in the present application, of five adjuvants tested, only a soluble phosphazene polymer (PCPP) provided full protection coupled with acceptable reactogenicity. Polyphosphazenes are additionally advantageous in that they can be delivered by a variety of methods, in particular by mucosal delivery, and as such need not be injected.

As used herein, the term "cat scratch disease" refers to the group of diseases most normally caused by the bacterium *B. henselae*. Some animals, e.g., the domestic cat, do not get a disease per se when infected with *B. henselae* and as such, "*B. henselae* infection" is used herein to denote infection with this bacterium, either with or without the subsequent development of detectable disease. As used herein, the term "to protect" includes, for example, to prevent or to treat (e.g., reduce or cure) *B. henselae* infection in the subject animal. As such, a therapeutic composition of the present invention can be a prophylactic vaccine or a treatment for animals already infected with the organism. The therapeutic composition can be used in a method to protect a subject animal from *B. henselae* infection by administering the therapeutic composition to that animal. The therapeutic composition can also be used in a method to protect a subject animal, e.g., a susceptible human, from cat scratch disease by administering the therapeutic composition to a carrier animal, e.g., a domestic cat in proximity with the subject animal, thereby preventing bacteremia in the carrier animal and subsequent transmission to the subject animal. Therapeutic compositions of the present invention can be administered to any animal susceptible to such therapy, preferably to mammals, and more preferably to felids and primates. Even more preferred animals to protect against *B. henselae* infection include wild cats, domestic cats and humans.

It is to be noted that the term "a" or "an" entity refers to one or more of that entity; for example, a *B. henselae* antigen refers to one or more *B henselae* antigens, or at least one *B. henselae* antigen. As such, the terms "a" (or "an"), "one or more" and "at least one" can be used interchangeably herein. It is also to be noted that the terms "comprising", "including", and "having" can be used interchangeably.

An isolated *B. henselae* antigen of the present invention is a *B. henselae* antigen that is removed from its natural milieu. As such, the term "isolated" does not describe any specific level of purity of the isolated antigen. A *B. henselae* antigen can be, for example, a whole-cell *B. henselae* (e.g., an intact cell or a composition comprising essentially all components of a cell, such as a whole-cell lysate) organism or any immunogenic fraction thereof. As used herein, the term immunogenic fraction refers to any portion of *B. henselae*, such as, but not limited to, any proteins, nucleic acids, carbohydrates, lipids, lipopolysaccharides, membranes, ghosts, cytoplasms, nuclei, cell walls, other bacterial fractions, that when administered to a subject animal, elicits an immune response in that animal.

*B. henselae* can be propagated by bacteriological methods well-known to those skilled in the art, examples of which are disclosed herein. For example, *B. henselae* can be grown upon a eukaryotic cell monolayer. Suitable eukaryotic cells upon which to grow *B. henselae* include monkey cells, human cells, mouse cells, cat cells and insect cells, with monkey cells being preferred. Preferred monkey cells upon which to grow *B. henselae* include Vero cells. *B. henselae* can also be grown on solid agar, such as on standard bacteriological agar plates, dishes or trays, for example, heart infusion agar supplemented with rabbit blood (HIA rabbit blood agar). *B. henselae* can also be growth in bacteriological broth suspension culture, for example, in supplemented Brucella broth.

*B. henselae* can be propagated at a variety of temperatures. A preferable growth temperature is from about 30° C. to about 39° C. More preferable is a growth temperature from about 32° C. to about 37° C.

One embodiment of an isolated *B. henselae* antigen is an inactivated *B. henselae* bacterium (i.e., an inactivated whole-cell *B. henselae* bacterium), which can be produced using standard inactivation techniques. For example, *B. henselae* inactivation can be accomplished by any one of the following treatments: formalin treatment, gamma-irradiation, UV irradiation, heat inactivation, beta-propiolactone inactivation, psorilen inactivation, or BEI inactivation. Preferred methods of inactivation include formalin treatment or heat inactivation. A more preferred method of inactivation is formalin treatment.

Preferred inactivated whole-cell *B. henselae* antigens include formalin-inactivated *B. henselae* grown on Vero cells, agar (e.g., agar plates) or broth culture. Preferred antigens include iBhV-Ag, iBhA-Ag and iBhB-Ag, the production of which is described in the Examples.

Another embodiment of the present invention is a live, whole-cell *B. henselae* antigen, a preferred embodiment of which can be produced by genetic modification of the organism, thereby rendering the organism unable to produce bacteremia in a mammal to which a therapeutic composition comprising such an antigen is administered.

In another embodiment, an isolated *B. henselae* antigen can be an immunogenic fraction of *B. henselae* bacteria. An immunogenic fraction can be recovered from the whole organism by chemical or mechanical disruption of the organism. The term "recovered", as well as similar phrases, refers to collection of the desired immunogenic fraction in which the *B. henselae* cells were grown and need not imply additional steps of separation or purification. For example, *B. henselae* cells can be subjected to detergent solubilization, e.g., with sodium dodecyl sulfate, Triton X-100®, a registered trademark of Union Carbide, or ethylphenyl-polyethylene glycol (NP-40®, Shell Oil Company), protein fractionation, protease treatment, freeze-thaw disruption, or sonication.

A *B. henselae* antigen can also be produced by recombinant means well known to those skilled in the art, and described in standard manuals such as Sambrook et al., 1989, *Molecular Cloning: A Laboratory Manual*, Cold Spring Harbor Labs Press; Sambrook et al., ibid., is incorporated by reference herein in its entirety. For example, an immunogenic fraction of the present invention can be obtained by synthesizing a vector comprising a nucleic acid sequence encoding an immunogenic fraction of *B. henselae*. The vector can then be placed in a host (e.g., a host cell to allow for production of a protein or a host to be immunized) wherein the immunogenic fraction of *B. henselae* will be synthesized. As a further embodiment, mixtures comprising a whole-cell *B. henselae* and immunogenic fractions thereof can be used in the present invention.

*B. henselae* antigens of the present invention can include any antigen, including homologs thereof, that, when administered to an animal as an immunogen, using techniques known to those skilled in the art, will produce a humoral, mucosal, and/or cellular immune response against *B. henselae* in that animal. As used herein, the term "homolog" refers to any closely related antigen or epitope capable of eliciting an immune response to the native antigen. Examples of homologs include *B. henselae* proteins in which amino acids have been deleted (e.g. a truncated version of the protein, such as a peptide), inserted, inverted, substituted, and/or derivatized (e.g., by glycosylation, phosphorylation, acetylation, myristylation, prenylation, palmitoylation, amidation and/or addition of glycerophosphatidyl inositol) such that the homolog includes at least one epitope capable of eliciting an immune response against *B. henselae*. As used herein, an epitope refers to the smallest portion of an antigen that is capable of eliciting an immune response in an animal. The minimal size of a protein epitope, as defined herein, is about five amino acids. It is to be noted, however, that such an epitope might comprise a portion of the antigen other than the amino acid sequence, e.g., a carbohydrate moiety or a lipid moiety. Furthermore, such an epitope can be discontinuous, i.e., it comprises amino acid residues that are not adjacent in the polypeptide, but are brought together into an epitope by way of the secondary or tertiary structure of the protein.

An immunogenic amount of an isolated *B. henselae* antigen, i.e., an amount that, when administered to an animal as an immunogen, will produce a humoral, mucosal, and/or cellular immune response against *B. henselae* in that animal, can be determined using standard procedures, examples of which are provided herein. Briefly, various concentrations of a selected isolated *B. henselae* antigen are prepared, mixed with a suitable adjuvant, and administered to animals. The animals are then challenged with an inoculum of infectious *B. henselae*, and are subsequently screened for bacteremia. The absence or reduction of bacteremia in such animals is an indication of the protective ability of the *B. henselae* antigen tested. Suitable doses of a whole-cell *B. henselae* antigen include at least about $1 \times 10^2$ *B. henselae* colony forming unit (CFU) equivalents per dose. A preferred dose comprises at least about $1 \times 10^4$ *B. henselae* CFU equivalents per dose, a more preferred dose comprises at least about $1 \times 10^5$ *B. henselae* CFU equivalents per dose, and an even more preferred dose comprises at least about $5 \times 10^6$ *B. henselae* CFU equivalents per dose. The maximum suitable dose is defined only by the practicalities of growing large quantities of *B. henselae*. According to methods described herein, the maximum practical dose is about $1 \times 10^8$ CFU equivalents. As used herein, the term "colony forming unit equivalents" or "CFU equivalents" refers to the plate titer of bacteria measured (prior to inactivation, if performed) of the whole-cell *B. henselae*. Methods to determine the plate titer are disclosed in the Examples.

In one embodiment, a therapeutic composition of the present invention can be multivalent, i.e., it can protect an animal from one or more other infectious agents in addition to *B. henselae*. Examples of multivalent therapeutic compositions include, but are not limited to, a *B. henselae* antigen of the present invention plus one or more antigens protective against one or more other infectious agents, such as, but not limited to: viruses, e.g., adenoviruses, caliciviruses, coronaviruses, distemper viruses, hepatitis viruses, herpesviruses, immunodeficiency viruses, infectious peritonitis viruses, leukemia viruses, oncogenic viruses, papilloma viruses, parainfluenza viruses, parvoviruses, rabies viruses, and reoviruses, as well as other cancer-causing or cancer-related viruses; bacteria, e.g., Actinomyces, Bacillus, Bacteroides, Bordetella, Bartonella, Borrelia, Brucella, Campylobacter, Capnocytophaga, Clostridium, Corynebacterium, Coxiella, Dermatophilus, Enterococcus, Elirlichia, Escherichia, Francisella, Fusobacterium, Haemobartonella, Helicobacter, Klebsiella, L-form bacteria, Leptospira, Listeria, Mycobacteria, Mycoplasma, Neorickettsia, Nocardia, Pasteurella, Peptococcus, Peptostreptococcus, Proteus, Pseudomonas, Rickettsia, Rochalimaea, Salmonella, Shigella, Staphylococcus, Streptococcus, and Yersinia; fungi and fungal-related microorganisms, e.g., Absidia, Acremonium, Alternaria, Aspergillus, Basidiobolus, Bipolaris, Blastomyces, Candida, Chlamydia, Coccidioides, Conidiobolus, Cryptococcus, Curvalaria, Epidermophyton, Exophiala, Geotrichum, Histoplasma, Madurella, Malassezia, Microsporum, Mon ilella, Mortierella, Mucor, Paecilomyces, Penicillium, Phialemonium, Phialophora, Prototheca, Pseudallescheria, Pseudomnicrodochium, Pythium, Rhinosporidium, Rhiizopus, Scolecobasidium, Sporotlirix, Stempylium, Trichophyton, Trichosporon, and Xylohypha; parasites, e.a., Babesia, Balantidium, Besnoitia, C typtosporidium, Eimeria, Encephalitozoon, Entamoeba, Giardia, Hammondia, Hepatozoon, Isospora, Leishmania, Micro sporidia, Neospora, Nosema, Pentatrichomonas, Plasmodium, Pneumocystis, Sarcocystis, Schistosoma, Theileria, Toxoplasma, and Trypanosoma, and helminth parasites, e .g., Acanthocheilonema, Aelurostrongylus, Ancylostoma, Angiostrongylus, Ascaris, Brugia, Bunostomum, Capillaria, Chabertia, Cooperia, Crenosorna, Dictyocaulus, Dioctophyme, Dipetalonema, Diphyllobothrium, Diplydium, Dirofilaria, Dracunculus, Enterobius, Filaroides, Haemonchus, Lagochilascaris, Loa, Mansonella, Muellerius, Naiophyetus, Necator, Neniatodirus, Oesophagostomum, Onchocerca, Opisthorchis, Ostertagia, Parafilaria, Paragonimus, Parascaris, Physaloptera, Protostrongylus, Setaria, Spirocerca, Spirometra, Stephanofilaria, Strongyloides, Strongylus, Thelazia, Toxascaris, Toxocara, Trichinella, Trichostrongylus, Trichuris. Uncinaria, and Wuchereria.

A therapeutic composition of the present invention comprises not only an isolated *B. henselae* antigen but also an adjuvant that comprises a phosphazene polymer. As used herein the term tadjuvant" refers to any compound capable of enhancing the immune response, i.e., improving the humoral, mucosal, or cellular immunity, of an animal to a specific antigen. Phosphazene polymers are also referred to herein as polyphosphazenes. As used herein, the terms are interchangeable. Polyphosphazenes are disclosed, for example, in U.S. Pat. No. 5,494,673, by Andrianov, et al., issued Feb. 27, 1996 (Andrianov '673); U.S. Pat. No. 5,550,161, by Andrianov, et al., issued Mar. 19, 1996 (Andrianov '161); and U.S. Pat. No. 5,529,777, by Andrianov, et al., issued Jun. 15, 1996 (Andrianov '777). Andrianov '673, ibid., Andrianov '161, ibid., and Andrianov '777, ibid. are incorporated herein by reference in their entireties.

Polyphosphazenes are polymers with backbones consisting of alternating phosphorus and nitrogen, separated by alternating single and double bonds. Each phosphorous atom is covalently bonded to two pendant groups ("R"). The repeat unit in polyphosphazenes has the following general formula:

$$-\left(\begin{array}{c} R \\ | \\ P = N \\ | \\ R \end{array}\right)_{\overline{n}}-$$

wherein n is an integer.

The substituent ("R") can be any of a wide variety of moieties that can vary within the polymer, including but not limited to aliphatic, aryl, aralkyl, alkaryl, carboxylic acid, heteroaromatic, carbohydrates, including glucose, heteroalkyl, halogen, (aliphatic)amino including alkylamino-, heteroaralkyl, di(aliphatic)amino- including dialkylamino-, arylamino-, diarylamino-, alkylarylamino-, -oxyaryl including but not limited to -oxyphenyl$CO_2H$, -oxyphenyl$SO_3H$, -oxyphenyl-hydroxyl and -oxyphenyl$PO_3H$; -oxyaliphatic including -oxyalkyl, -oxy(aliphatic)$CO_2H$, -oxy(aliphatic)$SO_3H$,-oxy(aliphatic)$PO_3H$, and -oxy(aliphatic)hydroxyl, including oxy(alkyl)hydroxyl; -oxyalkaryl, -oxyaralkyl, -thioaryl, thioaliphatic including -thioalkyl, -thioalkaryl, thioaralkyl, —NHC(O)O-(aryl or aliphatic), —O—[$(CH_2)xO$]y—$CH_2$—O—[$(CH_2)xO$]y$(CH_2)x$NH$(CH_2)x$SO$_3$H, and —O—[$(CH_2)xO$]y-(aryl or aliphatic), wherein x is 1–8 and y is an integer of 1 to 20. The groups can be bonded to the phosphorous atom through, for example, an oxygen, sulfur, nitrogen, or carbon atom.

In general, when the polyphosphazene has more than one type of pendant group, the groups will vary randomly throughout the polymer, and the polyphosphazene is thus a random copolymer. Phosphorous can be bound to two like groups, or two different groups. Polyphosphazenes with two or more types of pendant groups can be produced by reacting poly(dichlorophosphazene) with the desired nucleophile or nucleophiles in a desired ratio. The resulting ratio of pendant groups in the polyphosphazene will be determined by a number of factors, including the ratio of starting materials used to produce the polymer, the temperature at which the nucleophilic substitution reaction is carried out, and the solvent system used. While it is very difficult to determine the exact substitution pattern of the groups in the resulting polymer, the ratio of groups in the polymer can be easily determined by one skilled in the art.

In one embodiment, the adjuvant is a biodegradable polyphosphazene of the formula:

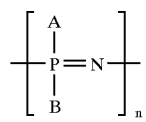

wherein A and B can vary independently in the polymer and can be (i) a group that is susceptible to hydrolysis under the conditions of use, including but not limited to chlorine, amino acid, amino acid ester (bound through the amino group), imidazole, glycerol, or glucosyl; or (ii) a group that is not susceptible to hydrolysis under the conditions of use, including, but not limited to an aliphatic, aryl, aralkyl, alkaryl, carboxylic acid, heteroaromatic, heteroalkyl, (aliphatic)amino- including alkylamino-, heteroaralkyl, di(aliphatic)amino including dialkylamino-, arylamino-, diarylamino-, alkylaryamino-, oxyaryl including but not limited to -oxyphenylCO$_2$H, -oxyphenyl SO$_3$H, -oxyphenylhydroxyl and -oxyphenylPO$_3$H; -oxyaliphatic including -oxyalkyl, -oxy(aliphatic)CO$_2$H, -oxy(aliphatic) SO$_3$H, -oxy(aliphatic)PO$_3$H, and -oxy(aliphatics)hydroxyl, including -oxy(alkyl)hydroxyl; -oxyalkaryl, -oxyaralkyl, -thioaryl, -thioaliphatic including -thioalkyl, -thioalkaryl, or thioaralkyl; wherein the polymer contains at least one percent or more, preferably 10 percent or more, and more preferably 80 to 90 percent or more, but less than 100%, of repeating units that are not susceptible to hydrolysis under the conditions of use, and wherein n is an integer of 4 or more, and preferably between 10 and 20,000 to 300,000. It should be understood that certain groups, such as heteroaromatic groups other than imidazole, hydrolyze at an extremely slow rate under neutral aqueous conditions, such as that found in the blood, and therefore are typically considered nonhydrolyzable groups for purposes herein. However, under certain conditions, for example, low pH, as found, for example, in the stomach, the rate of hydrolysis of normally nonhydrolyzable groups (such as heteroaromatics other than imidazole) can increase to the point that the biodegradation properties of the polymer can be affected. One of ordinary skill in the art using well known techniques can easily determine whether pendant groups hydrolyze at a significant rate under the conditions of use. One of ordinary skill in the art can also determine the rate of hydrolysis of the polyphosphazenes of diverse structures as described herein, and will be able to select that polyphosphazene that provides the desired biodegradation profile for the targeted use.

The degree of hydrolytic degradability of the polymer will be a function of the percentage of pendant groups susceptible to hydrolysis and the rate of hydrolysis of the hydrolyzable groups. The hydrolyzable groups are replaced by hydroxyl groups in aqueous environments to provide P—OH bonds that impart hydrolytic instability to the polymer.

In other embodiments, the adjuvant is (i) a nonbiodegradable polyphosphazene wherein none, or virtually none, of the pendent groups in the polymer are susceptible to hydrolysis under the conditions of use, or (ii) a completely biodegradable polyphosphazene wherein all the groups are susceptible to hydrolysis under the conditions of use.

Phosphazene polyelectrolytes are defined herein as polyphosphazenes that contain ionized or ionizable pendant groups that render the polyphosphazene anionic, cationic, or amphophilic. The ionic groups can be in the form of a salt, or, alternatively, an acid or base that is or can be at least partially dissociated. Any pharmaceutically acceptable monovalent cation can be used as a counterion of the salt, including but not limited to sodium, potassium, and ammonium. The phosphazene polyelectrolytes can also contain non-ionic side groups. The phosphazene polyelectrolyte can be biodegradable or nonbiodegradable under the conditions of use. The ionized or ionizable pendant groups are preferably not susceptible to hydrolysis under the conditions of use.

A preferred phosphazene polyelectrolyte is preferably biodegradable. The term biodegradable as used herein, means a polymer that degrades within a period that is acceptable in the desired application, typically less than about five years and most preferably less than about one year, once exposed to a physiological solution having a pH from about pH 6 to pH 8 at a temperature of approximately 25° C. to 35° C.

A preferred phosphazene polyelectrolyte polymer contains pendant groups that include carboxylic acid, sulfonic acid, or hydroxyl moieties. While the acidic groups are usually on nonhydrolyzable pendant groups, they can alternatively, or in combination, also be positioned on hydrolyzable groups. In one embodiment, the polymer is a poly(organophosphazene) that includes pendant groups that include carboxylic acid moieties that do not hydrolyze under the conditions of use and pendant groups that are susceptible to hydrolysis under the conditions of use.

A particularly preferred adjuvant of the present invention is a phosphazene polyelectrolyte having carboxylic acid groups as side chains as shown in the following formula:

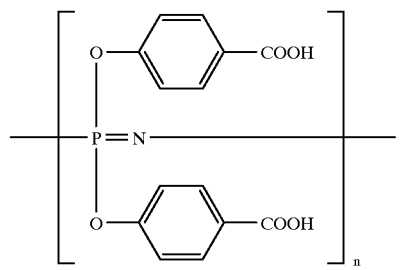

wherein n is an integer, preferably an integer between 10 and 10,000 to 300,000. This polymer has the chemical name poly[di(carboxylatophenoxy)phosphazene] or, alternatively, poly[bix(carboxylatophenoxy)phosphazene] (PCPP).

In one embodiment, an adjuvant comprising polyphosphazene is prepared as a microparticle. A microparticle refers to a solid particle typically ranging in size between approximately 1 and 1000 microns. Preferable microparticles for use in a therapeutic composition of the present invention range between approximately 1 and 10 microns in size. In this embodiment, polyphosphazene can be divalently crosslinked by combining a phosphazene polyelectrolyte with a metal multivalent cation such as zinc, calcium, bismuth, barium, magnesium, aluminum, copper, cobalt, nickel or cadmium. The polymer can then be coagulated to form microparticles by subjecting the formulation to impact forces, such as shearing forces in extrusion nozzles, high speed stirrers, colloid mills, or microfluidizers. The polymer can also be coagulated through the use of electrolytes, pH changes, organic solvents in low concentrations, or temperature changes. Details of these preparation methods and the use of such microparticles are found, for example, in Andrianov '161, ibid., and Andrianov '777, ibid., respectively.

A therapeutic composition of the present invention can comprise an isolated *B. henselae* antigen mixed with a soluble polyphosphazene formulation or a polyphosphazene microparticle. As used herein, the term "mixing" includes any method to combine the components of the therapeutic composition; such methods include, but are not limited to, blending, dispersing, dissolving, emulsifying, coagulating, suspending, or otherwise physically combining the components of the therapeutic composition. In one embodiment, a *B. henselae* antigen can be covalently linked to a phosphazene polymer.

In one embodiment, a *B. henselae* antigen of the present invention is microencapsulated into a polyphosphazene microparticle. As used herein, the term "microencapsulated" refers to the direct incorporation of the antigen into the microparticles. Methods to produce phosphazene polymers are disclosed, for example, in Andrianov '673, ibid., Andrianov '161, ibid., and Andrianov '777, ibid.

Particularly preferred therapeutic compositions of the present invention include (a) an isolated *B. henselae* antigen and a soluble form of PCPP, preferably a sodium salt of PCPP, (b) an isolated *B. henselae* antigen mixed with a PCPP microparticle; or (c) an isolated *B. henselae* antigen encapsulated in a PCPP microparticle.

A particularly preferred phosphazene polymer to use in the present invention is the soluble sodium salt of PCPP. A preferred amount of PCPP added to the therapeutic composition of the present invention is at least the smallest amount that is capable of enhancing an immune response to a *B. henselae* antigen. A particularly preferred amount of PCPP is the amount that maximally enhances an immune response to a *B. henselae* antigen without causing side effects (such as described in the Examples). A suitable amount of PCPP to use ranges from about 50 μg PCPP per dose to about 500 μg PCPP per dose. Preferred amounts of PCPP to use include 50 μg PCPP per dose, 100 μg PCPP per dose, 200 μg PCPP per dose, 400 μg PCPP per dose, and 500 μg PCPP per dose. Even more preferred amounts of PCPP to use are 50 μg PCPP per dose, 100 μg PCPP per dose, and 200 μg PCPP per dose.

In one embodiment of the present invention, the therapeutic composition includes one or more additional adjuvants. Additional adjuvants to include in the present invention include cytokines, chemokines, and compounds that induce the production of cytokines and chemokines, e.g., granulocyte macrophage colony stimulating factor (GM-CSF), granulocyte colony stimulating factor (G-CSF), macrophage colony stimulating factor (M-CSF), colony stimulating factor (CSF), erythropoietin (EPO), interleukin 2 (IL-2), interleukin 3 (IL-3), interleukin 4 (IL-4), interleukin 5 (IL-5), interleukin 6 (IL-6), interleukin 7 (IL-7), interleukin 8 (IL-8), interleukin 10 (IL-I0), interleukin 12 (IL-12), interferon gamma, interferon gamma inducing factor I (IGIF), transforming growth factor beta, RANTES (regulated upon activation, normal T-cell expressed and presumably secreted), macrophage inflammatory proteins (e.g., MIP-1 alpha and MIP-1 beta), and Leishmania elongation initiating factor (LeIF); bacterial components, e.g., endotoxins, in particular superantigens, exotoxins and cell wall components; aluminum-based salts; calcium-based salts; silica; polynucleotides; toxoids; serum proteins, viral coat proteins; block copolymer adjuvants, e.g., Hunter's Titermax™ adjuvant (Vaxcel™, Inc. Norcross, Ga.), Ribi adjuvants (Ribi ImmunoChem Research, Inc., Hamilton, Mont.); and saponins and their derivatives, e.g., Quil A (Superfos Biosector A/S, Denmark). Protein adjuvants of the present invention can be delivered in the form of the protein themselves or of nucleic acid molecules encoding such proteins.

A therapeutic composition of the present invention can be formulated in an excipient that the animal to be treated can tolerate. Examples of such excipients include water, saline, Ringer's solution, dextrose solution, Hank's solution, and other aqueous physiologically balanced salt solutions. Non-aqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer, and Tris buffer, while examples of preservatives include thimerosal,—or o-cresol, formalin, and benzyl alcohol. Standard formulations can either be liquids or solids which can be taken up in a suitable liquid as a suspension or solution for administration to an animal. Thus, in a non-liquid formulation, the excipient can comprise dextrose, human serum albumin, preservatives. etc., to which sterile water or saline can be added prior to administration.

In one embodiment of the present invention, a therapeutic composition can include a carrier. It should be noted, however, that a therapeutic composition of the present invention is advantageous in that it does not require an additional carrier. Carriers include compounds that increase the half-life of a therapeutic composition in the treated animal. Suitable carriers include, but are not limited to, polymeric controlled release vehicles (e.g., hydrogels), biodegradable implants, liposomes, bacteria, viruses, other cells, oils, esters, and glycols.

One embodiment of the present invention includes, in addition to a phosphazene polymer, one or more additional controlled release formulations that are capable of slowly releasing a composition of the present invention into an animal. As used herein, a controlled release formulation comprises a composition of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, lipospheres, and transdermal delivery systems. Other controlled release formulations of the present invention include liquids that, upon administration to an animal, form a solid or a gel in situ. Preferred controlled release formulations are biodegradable (i.e., bioerodible).

A preferred controlled release formulation of the present invention is capable of releasing a composition of the present invention into the blood of the treated animal at a constant rate sufficient to attain therapeutic dose levels of the composition to protect an animal from infection by or disease caused by *B. henselae*. The therapeutic composition is preferably released over a period of time ranging from about 1 to about 12 months. A controlled release formulation of the present invention is capable of effecting a treatment preferably for at least about 1 month, more preferably for at least about 3 months, even more preferably for at least about 6 months, even more preferably for at least about 9 months, and even more preferably for at least about 12 months.

Preferred therapeutic compositions of the present invention include soluble PCPP mixed with a whole-cell *B. henselae* antigen, preferably an inactivated whole-cell *B. henselae* antigen, and more preferably iBhV-Ag, iBhA-Ag or iBhB-Ag. An even more preferred therapeutic composition includes any one of the above *B. henselae* antigens blended with at least about 50 µg/ml PCPP.

The present invention also includes methods to protect a mammal from *B. henselae* infection using a therapeutic composition of the present invention. Acceptable protocols to administer therapeutic compositions in an effective manner include individual dose size, number of doses, frequency of dose administration, and mode of administration. Determination of such protocols can be accomplished by those skilled in the art. A suitable single dose is a dose that is capable of protecting an animal from disease when administered one or more times over a suitable time period. Booster vaccinations can be administered from about 2 weeks to several years after the original administration. Booster administrations preferably are administered when the immune response of the animal becomes insufficient to protect the animal from disease. Examples of suitable and preferred dosage schedules are disclosed in the Examples section. A therapeutic composition of the present invention can be administered to an animal by a variety of means. Such means include, but are not limited to, injection (including intradermal, subcutaneous and intramuscular injection), oral administration, intranasal administration, intraocular administration, transdermal administration, topical administration, or administration by a mechanical means such as a Biojector™ or a gene gun.

The efficacy of a therapeutic composition of the present invention to protect an animal from *B. henselae* infection can be tested in a variety of ways including, but not limited to, detection of protective antibodies, detection of cellular immunity within the treated animal, or challenge of the treated animal with live *B. henselae* to determine whether the treated animal is resistant to the development of bacteremia.

The present invention also includes methods to produce a therapeutic composition of the present invention. Suitable and preferred methods for making a therapeutic composition of the present invention are disclosed herein. The pertinent steps involved in producing a therapeutic composition of the present invention include: a) growing *B. henselae* cells by a method such as those described herein; b) preparing an isolated *B. henselae* antigen, for example, by inactivating the cells, disrupting the cells, fractionating the cells, or attenuating the cells; and c) mixing the isolated *B. henselae* antigen with a phosphazene polymer of the present invention.

The following examples are provided for the purposes of illustration and are not intended to limit the scope of the present invention.

EXAMPLES

It is to be noted that the Examples include a number of microbiology and immunology techniques considered to be known to those skilled in the art. Disclosure of such techniques can be found, for example, in Prescott, et al., *Microbiology*, 3$^{rd}$ Edition, Wm. C. Brown and Company; and Harlow, et al., 1988, *Antibodies, a Laboratory Manual*, Cold Spring Harbor Labs Press. Prescott, et al., ibid. and Harlow et al., ibid., are each incorporated by reference herein in its entirety.

Example 1

This Example describes the preparation and formulation of *B. henselae* antigen for use in the vaccination of cats against *B. henselae* infection.

A. Preparation and formulation of Vero cell-grown *B. henselae* antigen. *B. henselae* was cultivated on Vero cells by the following method. Vero cells (available as Catalog No. ATCC CRL-1586 from the American Type Culture Collection (ATCC), 10801 University Boulevard, Manassas, Va. 20110–2209 were cultured to near-confluency in 150-cm$^2$ tissue culture flasks in medium comprising MEM supplemented with fetal bovine serum (10%), L-glutamine (2 mM), non-essential amino acids (0.1 mM), and HEPES buffer (10 mM) (all components available from Life Technologies, Inc., Gaithersburg, Md.). This medium formulation is referred to herein as MEMsuppl. The adherent cultured Vero cells were washed twice with sterile phosphate buffered saline (PBS), and then 10 ml of MEMsuppl was added to each flask. A 100-µl aliquot of a *B. henselae* stock culture, comprising about 1×10$^8$ CFU per ml, was added to each flask, and the inoculated medium was mixed such that it covered the cell monolayer. The inoculated flasks were incubated at about 32° C. for one hour, and the flasks were rocked manually every 15 minutes during this incubation period to allow the *B. henselae* bacteria to attach to the Vero cells. Following the one-hour incubation period, 40 ml of MEMsuppl was added to each flask, and the *B. henselae*-infected cells were incubated for 7 days at about 32° C. in a CO$_2$ (5%) incubator. Following growth of the bacteria, the flasks were frozen at −70° C. prior to further manipulations.

The Vero cell-grown cultures of *B. henselae* were harvested and concentrated as follows. The tissue culture flasks containing *B. henselae* grown on Vero cells were thawed, and the cell monolayers were dislodged from the flasks by vigorously tapping each flask against the palm of one hand. Media and cells from the thawed flasks were transferred to 250-ml sterile centrifuge bottles, and cells and bacteria were centrifuged at about 5306×g for 30 minutes at 5° C. using, for example, a Sorvall™ RCSC centrifuge fitted with an HS-4 rotor (available from Sorvall, Newtown, Conn.) set at 5000 RPM. The cell pellets were resuspended in a total of 2 ml MEMsuppl per flask of cells. The cell pellet was resuspended by gentle pipetting. The antigen preparation (containing *B. henselae* cells and disrupted Vero cells) was then further disrupted by drawing the material in and out of a 20-ml syringe fitted with a blunt-ended 18 gauge needle several times until the preparation appeared homogeneously dispersed. The resulting composition is referred to herein as *B. henselae* Vero-derived antigen, or BhV-Ag. Two 100-µl aliquots of the BhV-Ag pool were titrated on heart infusion agar (HIA, available from Becton Dickinson, Sparks, Md.) supplemented with 5% rabbit blood (referred to herein as HIA rabbit blood agar) by methods similar to those described in Example 1 of Anderson et al, '485, ibid. The titration results were used to calculate the CFU equivalents of the inactivated antigen preparations, prepared as described below.

BhV-Ag was formalin-inactivated by the following method. BhV-Ag, made as described above, was mixed with formaldehyde (37% aqueous solution, available from Mallinckrodt, Chesterfield, Mo.) to reach a final concentration of 0.25% formalin (vol/vol), e.g., 0.20 ml of formaldehyde solution was added to 80 ml of BhV-Ag. The BhV- Ag/formalin mixture was incubated at about 35° C. for 24 hours with occasional mixing to inactivate the live *B. henselae* bacteria. After the 24-hour incubation, free formalin was neutralized by the addition of a volume of 50% (wt/vol) sodium bisulfite equal to volume of formaldehyde solution added earlier, e.g., 0.2 ml of sodium bisulfite solution was added to the 80.2 ml formnalin/BhV-Ag solution. A 100-μl aliquot of the inactivated BhV-Ag (referred to herein as iBhV-Ag) was cultured on HIA rabbit blood agar as described above to ensure that all *B. henselae* organisms were inactivated. The remainder of the iBhV-Ag pool was stored at 4° C. until further use.

A vaccine composition comprising iBhV-Ag and a polyphosphazene adjuvant was prepared as follows. The iBhV-Ag pool, prepared as described above, was allowed to come to room temperature, and was mixed thoroughly prior to removal of aliquots for mixing with the adjuvant. A soluble adjuvant formulation comprising 1000 μg of the sodium salt of poly[di(carboxylatophenoxy)phosphazene] (also referred to herein as PCPP and described for example, in Andrianov et al., '673, ibid.) per ml of sterile PBS (0.1% wt/vol), was similarly allowed to reach room temperature. Appropriate dilutions of the PCPP solution (in sterile PBS) were mixed at a 1:1 ratio with a constant amount of iBhV-Ag to achieve concentrations of 500 μg PCPP/ml (0.05% wt/vol), 200 μg PCPP/ml (0.02% wt/vol), 100 μg PCPP/ml (0.01% wt/vol), and 50 μg PCPP/ml (0.005% wt/vol), as needed, for the various vaccination protocols described in Examples 2–4 below. The resulting mixtures were then thoroughly blended by vortexing for 1–2 minutes. The resulting vaccine formulations were then placed into sterile vials with rubber stoppers. A 100-μl aliquot was taken from each vial and plated onto HIA rabbit blood agar for sterility testing according to standard methods.

B. Preparation of agar-grown *B. henselae* antigen. Agar-grown *B. henselae* antigen was prepared as follows. HIA rabbit blood agar plates were inoculated with 100 μl each of a *B. henselae* stock culture, produced as described in Section A. The inoculum was evenly distributed over the entire agar surface using a sterile inoculation loop. The inoculated plates were sealed into plastic bags and were incubated at about 32° C. with 5% $CO_2$ for about 5–8 days, until the colonies were small pinpoint size but were not too deeply imbedded in the agar. The colonies were harvested by placing 5 ml of brain-heart infusion broth (BHI, available from Becton Dickinson) onto the agar surface of each plate and scraping the colonies into the broth using a sterile inoculation loop. The harvested material from all plates was pooled and clumps were homogenized by passage through a blunt-ended 18 gauge needle as described in Section A. The *B. henselae* pool was titrated on HIA rabbit blood agar plates by standard methods as described in Section A. The antigen, referred to herein as BhA-Ag, was formalin-inactivated by the method described for BhV-Ag in Section A, and the resultant inactivated antigen pool, referred to herein as iBhA-Ag, was stored at 4° C. until used. A vaccine formulation comprising iBhA-Ag and PCPP was prepared as described in Section A for the formulation iBhV-Ag and PCPP.

C. Preparation and formalin-inactivation of broth-grown *B. henselae* antigen. Broth-grown *B. henselae* antigen was prepared as follows. The base nutrient broth was Brucella broth, available from Difco Laboratories, Detroit, Mich. This broth base was mixed into distilled water at 2× concentration, and the broth was sterilized by autoclaving for about 15–30 minutes. Following sterilization of the above medium, the following additives were added from sterile stock solutions to the final concentrations shown:

| | |
|---|---|
| Soluble Starch | 5 g per liter |
| Hemin | 0.015 g per liter |
| Asparagine | 0.05 g per liter |
| Alpha-keto glutaric acid | 0.05 g per liter |
| Sodium citrate | 0.05 g per liter |
| Glutamic acid | 0.05 g per liter |
| Succinic acid | 0.05 g per liter |

Sufficient sterile distilled water was added to bring the broth to 1× concentration. The resultant broth composition is referred to herein as MJ35 medium.

To prepare a starter culture of *B. henselae*, 800 ml of 1×MJ35 medium was prepared, and approximately 350 ml was added to each of two sterile 1000-ml splined flasks. To each flask, an inoculum of *B. henselae* comprising about $1 \times 10^6$ CFU per ml was added. The flasks were incubated at 32° C. with 5% $CO_2$ on a shaker platform set at about 80 rpm. The flasks were monitored for growth by measuring the optical density at 600 nm ($OD_{600}$) in a spectrophotometer, for example a Spec20™, available from Fisher Scientific, Pittsburgh, Pa. Total growth time for these flasks was about 55–60 hours to reach an $OD_{600}$ of about 0.15–0.20. In the meantime, 1×MJ35 medium was prepared. A 7.5-liter fermentation flask, for example, a Magnaform vessel (available from New Brunswick Scientific, Edison, N.J.), was assembled, was filled halfway with distilled water, and was sterilized by autoclaving. After cooling, the fermentation vessel was attached to the fermentation unit and the water was pumped out. Immediately thereafter, about five (5) liters of MJ35 medium was added to the vessel. About 450 ml of the starter culture was added to a 500-mi drop bottle. In addition, 0.1 ml of an antifoaming agent, for example, SAG 471 (available from Osi Specialties, Danbury, Conn.) was added to the drop bottle. The drop bottle was aseptically connected to the fermentor vessel and the contents were fed into the vessel by gravity. The agitation of the vessel was set at 100 rpm and the aeration was set to 5% $CO_2$ in air. The fermentor vessel was maintained at about 32° C. The Fernbach flasks and the fermentor vessel were periodically monitored for growth by measuring the $OD_{600}$ of aliquots removed from the containers. These aliquots were also titrated for plate counts on TSA agar (available from Difco) supplemented with 5% rabbit blood (sheep blood may also be used) as described in Section A. Following growth for approximately 25–35 hours (to approximately an $OD_{600}$ of 0.15–0.20, and a plate count of about $1–5 \times 10^8$ CFU per ml), the *B. henselae* cells were concentrated by centrifugation. The centrifuged cell pellets were resuspended in a total of about 100–150 ml of 50% RPMI medium without phenol red and sodium bicarbonate (available from Life Technologies, Inc., Gaithersburg, Md.). A sample of the concentrated *B. henselae* cells was taken for plate counts and for total counts using a Petroff-Hauser counting cell. The resultant antigen, referred to herein as BhB-Ag, was formalin-inactivated by the method described for BhV-Ag in Section A, and the resultant inactivated antigen pool, referred to herein as iBhB-Ag, was stored at 4° C. until used. A vaccine formulation comprising iBhB-Ag and PCPP was prepared as described in Section A for the formulation iBhV-Ag and PCPP.

Example 2

This example discloses the protective efficacy of a vaccine formulation of the present invention comprising iBhV-Ag mixed with PCPP relative to iBhV-Ag mixed with a variety of other adjuvants. This animal study evaluates (a) the protective efficacy of iBhV-Ag in combination with several different adjuvant formulations; (b) the relative effectiveness of different adjuvants; and (c) the relative reactogenicity of different adjuvants.

The B. henselae antigen iBhV-Ag was prepared as described in Example 1, Section A.

This study consisted of 69 SPF (specific pathogen free) cats, including 64 test cats purchased from a licensed supplier of SPF laboratory cats (e.g., Harlan Sprague-Dawley, Madison, Wis.) and 5 positive control cats (i.e., cats recovered from a previous B. henselae infection) selected from cats previously infected with B. henselae at the Centers for Disease Control, Atlanta, Ga. (CDC). The animals were housed in isolation facilities at CDC for the duration of the test.

The cats were assigned to 9 groups, as follows. Group 1 (n=10) was given $1.6 \times 10^6$ CFU equivalents of iBhV-Ag blended with 500 µg PCPP/ml (0.05% wt/vol), formulated as described in Example 1 above; Group 2 (n=10) was given $1.6 \times 10^6$ CFU equivalents of iBhV-Ag blended with 0.25% Carbopol® (available from BF Goodrich, Cleveland, Ohio); Group 3 (n=10) was given $1.6 \times 10^6$ CFU equivalents of iBhV-Ag blended with 1 mg/ml dimethyl dioctadecyl ammonium bromide (DDA, available from Fluka Chemical Company, Milwaukee, Wis.); Group 4 (n=10) was given $1.6 \times 10^6$ CFU equivalents of iBhV-Ag blended with 25 mg/ml block copolymer CRL-8623 (obtained from VetLife, Norcross, Ga.); Group 5 (n=8) was given $1.6 \times 10^6$ CFU equivalents of iBhV-Ag blended with 180 µg/ml M40 ISCOM (obtained from the CDC); Group 6 (n=8) was given $1.6 \times 10^6$ CFU equivalents of iBhV-Ag blended with 50 µg/ml Leishmania elongation initiation factor (LeIF) (obtained from Corixa Corp., Seattle, Wash.); Group 7 (n=3) was given $1.6 \times 10^6$ CFU equivalents of iBhV-Ag without adjuvant; Group 8, the challenge control cats (n=5), were given uninfected, formalin-inactivated Vero cells prepared according to the same method used to prepare iBhV-Ag as described in Example 1, section A, except the Vero cells were not inoculated with B. henselae; and Group 9, (n=5) consisted of the cats that had recovered from a previous challenge, and were included as positive controls. All groups receiving experimental or control vaccine formulations were given two subcutaneous doses of 1 ml each, with a three week interval between doses. Two weeks after the second vaccination, all cats were challenged by subcutaneous inoculation of $10^4$ CFU live *B. henselae* organisms, grown on agar essentially as described in Example 1, Section B above, except that instead of homogenizing the harvested bacterial colonies by needle aspiration, large clumps were allowed to settle out and the relatively homogeneous supernatant was decanted. The challenge inoculum was diluted to 1×105 CFU/ml in BHI broth and the animals were challenged with 0.1 ml of this preparation. Bacteremia was monitored weekly for 12 weeks post challenge to determine the ability of the treatment to protect against bacteremia.

The cats were observed for approximately 30 minutes immediately following and at approximately four hours after each inoculation for immediate type reactions, including pain on injection (vocalization, looking at site, scratching the site of inoculation), salivation, labored or irregular breathing, shaking, or anaphylaxis. In addition, the cats were monitored for fever at four hours and twenty-four hours after inoculation. The cats were monitored daily for two weeks after each inoculation for delayed type reactions, including lethargy, anorexia, soreness at the injection site, swelling, granuloma, abscess or edema. The injection sites were palpated to determine soreness and/or pain on palpation. For any cat in which an increased body temperature was observed at four or twenty-four hours, the temperature continued to be monitored at each daily observation until the temperature returned to normal.

EDTA whole blood (for culturing) was collected prior to challenge, and once a week for 12 weeks after challenge. Blood samples were frozen immediately after collection. Frozen blood samples were later thawed then cultured on HIA rabbit blood agar as follows. Three ten-fold serial dilutions of each blood sample were made in BHI broth. A 100-μl aliquot of each dilution was applied to an individual agar plate by distributing the inoculum in about 2–3 drops and holding the plate at an approximate 60° angle so that the drops ran down the agar surface without reaching the rim of the plate. The culture plates were sealed into plastic bags and placed at 32° C. and 5% $CO_2$ for about 1 week. If no growth was seen, the plates were further incubated for at least 5 weeks before scoring as negative.

The results of this animal study are presented in Table 1.

TABLE 1

| | | | | | Reactions after 1st Vacc | | | Reactions after 2nd Vacc | | |
|---|---|---|---|---|---|---|---|---|---|---|
| Group | Treatment | Adjuvant | No. Cats | Bacteremic | Thickening † | Swelling ‡ | Total | Thickening | Swelling | Total |
| 1 | $1.6\times10^6$ CFU | 500 ug PCPP | 10 | 1 | — | 7 | 7/10 | 1 | 9 | 10/10 |
| 2 | *B. henselae* | .025% Carbopol | 10 | 3 | — | 10 | 10/10 | 1 | 4 | 5/10 |
| 3 | (grown in Vero | 1 mg DDA | 10 | 4 | — | 5 | 5/10 | — | 8 | 8/10 |
| 4 | cells; formalin | 25 mg copolymer | 10 | 5 | — | 1 | 1/10 | — | 7 | 7/10 |
| 5 | inactivated) | ISCOM | 8 | 5 | — | — | 0/8 | — | 3 | 3/8 |
| 6 | | 50 ug LeIF | 8 | 3 | — | — | 0/8 | — | — | 0/8 |
| 7 | | none | 3 | 1 | — | — | 0/3 | 1 | — | 1/3 |
| 8 | Media control* | none | 5 | 5 | — | — | 0/5 | 1 | — | 1/5 |
| 9 | Recovered (previous infection) | | 5 | 0 | | NA | | | NA | |

*Media control was Vero cells in medium only
† Thickening of skin over inoculation site, with no soft tissue swelling or nodule
‡ Soft tissue swelling or nodule The following number of cats experienced bacteremia following challenge with *B. henselae*: Group 1, 1/10 cats; Group 2, 3/10 cats; Group 3, 4/10 cats; Group 4, 6/10 cats; Group 5, 5/8 cats; Group 6, 3/8 cats; Group 7, 1/3 cats; Group 8, 5/5 cats; and Group 9, 0/5 cats. Of the groups receiving iBhV-Ag with adjuvant, Group 1, the cats receiving iBhV-Ag with 500 μg/ml PCPP, were the best-protected.

Table 1 also shows the vaccination site reactions observed after the first and second vaccinations among the various experimental groups. Except for Group 6, those cats receiving iBhV-Ag with the LeIF adjuvant, vaccination site reactions were observed to varying degrees among all the vaccinated groups. Although the PCPP adjuvant afforded the best protection among the adjuvants tested, most of the animals in the PCPP group experienced injection site swelling after both the first and second vaccinations.

Example 3

This example discloses an animal study demonstrating the protective efficacy of a vaccine formulation comprising iBhV-Ag mixed with PCPP at a lower concentration, a formulation which exhibited no injection site reactions. Furthermore, this study evaluated the efficacy and reactogenicity of vaccine formulations comprising iBhV-Ag in combination with LeIF at various concentrations.

As shown in Example 2, a vaccine formulation comprising iBhV-Ag and 500 $\mu$lg/ml PCPP adjuvant afforded the best protection among the adjuvants tested, but caused significant injection site reactions in the vaccinated animals. This study was initiated, in part, to examine whether a vaccine formulation comprising iBhV-Ag and a smaller amount of PCPP would be effective in protecting against *B. henselae* bacteremia in cats, while at the same time eliminating injection site reactions. In addition, this study examined whether higher amounts of LeIF adjuvant (which showed no injection site reactions in the previous study) could improve the immunogenicity of iBhV-Ag/LeIF formulations.

The *B. henselae* antigens iBhV-Ag and iBhA-Ag were prepared as described in Example 1, Sections A and B, respectively.

The study consisted of 68 SPF cats, including 63 test cats purchased from a licensed supplier of SPF laboratory cats and 5 positive control cats (i.e., cats recovered from a previous *B. henselae* infection) selected from cats previously infected with *B. henselae* at the CDC. The animals were housed in isolation facilities at CDC for the duration of the test.

The experimental design was identical to that described in Example 2, but with the following groups of cats: Group 1 (n=9) received $2.0\times10^7$ CFU equivalents of iBhV-Ag mixed with 500 $\mu$g PCPP/ml; Group 2 (n=9) received $2.0\times10^7$ CFU equivalents of iBhV-Ag mixed with 50 $\mu$g PCPP/ml; Group 3 (n=9) received $2.0\times10^7$ CFU equivalents of iBhV-Ag mixed with 250 $\mu$g LeIF/mL; Group 4 (n=9) received $2.0\times10^7$ CFU equivalents of iBhV-Ag mixed with 50 $\mu$g LeIF/ml; Group 5 (n=9) received $2.0\times10^7$ CFU equivalents of iBhV-Ag mixed with 10 $\mu$g LeIF/ml; Group 6 (n=6) received 2.0 $\times10^7$ CFU equivalents of iBhV-Ag with no added adjuvant; Group 7 (n=8) received $2.0\times10^7$ CFU equivalents of iBhA-Ag (prepared as disclosed in Example 1, Section B) with no added adjuvant; Group 8 (n=4) received uninfected Vero cells prepared according to the same method used to prepare BhV-Ag as described in Example 1, Section A, except the Vero cells were not inoculated with *B. henselae*; and Group 9, (n=5) consisted of the cats that had recovered from a previous challenge.

Observations and sample collections were carried out as described in Example 2.

The results of this animal study are presented in Table 2.

TABLE 2

| Group | Treatment | Medium | Adjuvant | No. Cats | Bacteremic | Reactions 1st vacc | Reactions 2nd vacc |
|---|---|---|---|---|---|---|---|
| 1 | $2.0 \times 10^7$ CFU | Vero cells | 500 ug PCPP | 9 | 0 | 7 ‡ | 7 |
| 2 | *B. henselae* | | 50 ug PCPP | 9 | 1 | 0 | 0 |
| 3 | (formalin inactivated) | | 250 ug LeIF | 9 | 2 | 0 | 0 |
| 4 | | | 50 ug LeIF | 9 | 4 | 0 | 0 |
| 5 | | | 10 ug LeIF | 9 | 4 | 0 | 0 |
| 6 | | | none | 6 | 2 | 0 | 0 |
| 7 | | Agar | none | 8 | 4 | 0 | 0 |
| 8 | Media control | Vero cells | none | 4 | 4 | 0 | 0 |
| 9 | Recovered (previous infection) | | NA | 5 | 0 | NA | |

‡ nodules up to 2.5 cm diameter

The following number of cats experienced bacteremia upon challenge with *B. henselae*. Group 1, 0/9 cats; Group 2, 1/9 cats; Group 3, 2/9 cats; Group 4, 4/9 cats; Group 5, 4/9 cats; Group 6, 2/6 cats; Group 7, 4/8 cats; Group 8, 4/4 cats; and Group 9, 0/5 cats. Both groups receiving iBhV-Ag with PCPP adjuvant were well protected. The onset of bacteremia in the one bacteremic cat in Group 2 occurred much later than seen in the first study disclosed in Example 2, as well as in the other experimental groups in this study. The cats in Group 1 and in Group 2 were further tested for recrudescence. The cats (except for the one cat in Group 2 that was bacteremic) were given 2.2 mg/kg prednisone daily for 14 days starting at week 15 after challenge, and blood cultures were tested weekly until week 19. The cats remained abacteremic throughout this treatment.

Among the groups that received iBhV-Ag with the LeIF adjuvant, the protective efficacy improved in the group receiving iBhV-Ag mixed with 250 $\mu$g/ml LeIF. No significant protective advantage was seen in using iBhA-Ag alone rather than iBhV-Ag alone.

Table 2 also shows the vaccination site reactions observed after the first and second vaccinations among the various experimental groups. As can be seen in Group 2, the injection site reactions observed with PCPP were totally eliminated by lowering the PCPP content of the vaccine formulation to 50 $\mu$g PCPP/ml without significantly altering the protective efficacy. No injection site reactions were seen in any of the groups receiving BhV-Ag mixed with LeIF (Groups 3–5).

Example 4

This example discloses an animal study further demonstrating the protective efficacy of vaccine formulations comprising iBhV-Ag in combination with various concentrations of PCPP.

Since no reactogenicity was seen in the cats vaccinated with iBhV-Ag mixed with 50 $\mu$g/ml PCPP (Group 2 in Example 3), and 8/9 of the animals in this group were fully protected, this study was initiated to determine the protective efficacy and relative reactogenicity of vaccine formulations comprising iBhV-Ag and PCPP added at concentrations between 50 μg/ml and 500 μg/ml.

The B. henselae antigen iBhV-Ag was prepared as described in Example 1, Section A.

This study consisted of 52 SPF cats, including 47 test cats purchased from a licensed supplier of SPF laboratory cats and 5 positive control cats (cats recovered from a previous B. henselae infection) selected from cats previously infected and held at Diamond Animal Health, Des Moines, Iowa. The animals were housed in isolation facilities at Diamond for the duration of the test.

The cats (except for the positive controls) were randomly assigned to 8 experimental groups, as follows. Group 1 (n=10) received $1.0 \times 10^7$ CFU equivalents of iBhV-Ag blended with 500 μg PCPP/ml; Group 2 (n=10) received $1.0 \times 10^7$ CFU equivalents of iBhV-Ag blended with 200 μg PCPP/ml; Group 3 (n=10) received $1.0 \times 10^7$ CFU equivalents of iBhV-Ag blended with 100 μg PCPP/ml; Group 4 (n=10) received $1.0 \times 10^7$ CFU equivalents of iBhV-Ag blended with 50 μg PCPP/ml; Group 5 (n=7), the media controls, received uninfected Vero cells prepared according to the same method used to prepare BhV-Ag as described in Example 1, Section A, except the Vero cells were not inoculated with B. henselae; and Group 6 (n=5) consisted of the cats that had recovered from a previous challenge. Blood was collected and tested for the presence of antibodies to B. henselae before the cats were vaccinated. The vaccinated groups (i.e., Groups 1–5) were given two doses of the respective vaccine or media control formulations by subcutaneous injection of 1 ml each, with a three week interval between doses. Three weeks after the second vaccination, all cats were challenged by subcutaneous inoculation of $10^4$ CFU live B. henselae organisms grown on agar as described in Example 1.

Observations and sample collections were carried out identically as described in Example 2.

The results of this animal study are presented in Table 3.

significantly altering the protective efficacy. Lower numbers of injection site reactions were seen with vaccine formulations comprising 100 μg/ml or 200 μg/ml PCPP than were seen with the formulation comprising 500 μg/ml PCPP. Injection site reactions were seen in the vaccinated groups following the second vaccination, with there being a direct correlation between PCPP concentration and the number of injection site reactions per group.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. A therapeutic composition to protect a mammal from Barionella henselae (B. henselae) infection, said composition comprising:
   (a) an isolated B. henselae antigen comprising whole inactivated B. henselae cells; and
   (b) an adjuvant comprising poly(di(carboxylatophenoxy) phosphazene) (PCPP).

2. The composition of claim 1, wherein said B. henselae cells are grown on agar.

3. The composition of claim 1, wherein said B. henselae cells are grown on eukaryotic cells, said cells being selected from the group consisting of Vero cells, cat cells, mouse cells, and human cells.

4. The composition of claim 1, wherein said B. henselae cells are grown in broth suspension culture.

5. The composition of claim 1, wherein said cells are inactivated by a method selected from the group consisting of formalin inactivation, gamma-irradiation, heat inactivation, beta-propiolactone inactivation, ultraviolet (UV) irradiation, psorilen inactivation, and binary ethylenimine (BEI) inactivation.

6. The composition of claim 1, wherein said PCPP is a microparticle.

7. The composition of claim 1, wherein said PCPP is a microparticle having said isolated B. henselae antigen microencapsulated therein.

TABLE 3

| | | | | | | --No. of cats with--Reactions | |
|---|---|---|---|---|---|---|---|
| Group | Treatment | PCPP | No. Cats | Challenge ‡ | Bacteremic | 1st vacc | 2nd vacc |
| 1 | $1.0 \times 10^7$ CFU | 500 μg | 10 | Agar grown | 0 | 4 † | [0]--9-- |
| 2 | B. henselae | 200 μg | 10 | | 1 | 2 | [0]--3-- |
| 3 | (Vero grow, formalin inact) | 100 μg | 10 | | 0 | [2]--1-- | [0]--3-- |
| 4 | | 50 μg | 10 | | 0 | 0 | [0]--1-- |
| 5 | Media control* | none | 7 | | 7 | [1]--0-- | 0 |
| 6 | Recovered (previous infection) | | 5 | | 0 | NA | |

*Media control was Vero cells in medium only
† skin thickness [>]--≧--4 mm change from baseline
‡ All cats were given $10^4$ CFU B. henselae The following percentage of cats experienced bacteremia upon challenge with B. henselae. Group 1, 0/10 cats; Group 2, 1/10 cats; Group 3, 0/10 cats; Group 4, 0/10 cats; Group 5, 7/7 cats;; and Group 6, 0/5 cats. All groups receiving iBhV-Ag with PCPP adjuvant were well protected.

Table 3 also shows the vaccination site reactions observed after the first and second vaccinations among the various experimental groups. In Group 4, the injection site reactions observed with PCPP again were totally eliminated by lowering the PCPP content of the vaccine to 50 μg/ml without 8. The composition of claim 1, wherein said composition further comprises a component selected from the group consisting of an excipient, a carrier, and an additional adjuvant.

9. The composition of claim 1, comprising:
   (a) a B. henselae antigen selected from the group consisting of iBhV-Ag, iBhA-Ag, and iBhB-Ag; and
   (b) an adjuvant comprising PCPP.

10. The composition of claim 1, wherein said mammal is selected from the group consisting of felids and primates.

11. The composition of claim 1, wherein said mammal is selected from the group consisting of domestic cats and humans.

12. A method to protect a mammal from *B. henselae* infection comprising administering to said mammal a therapeutic composition comprising:
   (a) an isolated *B. henselae* antigen comprising whole inactivated *B. henselae* cells; and
   (b) an adjuvant comprising PCPP.

13. The method of claim 12, wherein said *B. henselae* cells are grown on agar.

14. The method of claim 12, wherein said *B. henselae* cells are grown on eukaryotic cells, said cells being selected from the group consisting of Vero cells, cat cells, mouse cells, and human cells.

15. The method of claim 12, wherein said *B. henselae* cells are grown in broth suspension culture.

16. The method of claim 12, wherein said cells are inactivated by a method selected from the group consisting of formalin inactivation, gamma-irradiation, heat inactivation, beta-propiolactone inactivation, UV irradiation, psorilen inactivation, and BEI inactivation.

17. The method of claim 12, wherein said PCPP is a microparticle.

18. The method of claim 12, wherein said PCPP is a microparticle having said isolated *B. henselae* antigen microencapsulated therein.

19. The method of claim 12, wherein said composition further comprises a component selected from the group consisting of an excipient, a carrier, and an additional adjuvant.

20. The method of claim 12, wherein said therapeutic composition comprises:
   (a) a *B. henselae* antigen selected from the group consisting of iBhV-Ag, iBhA-Ag, and iBhB-Ag; and
   (b) an adjuvant comprising PCPP.

21. The method of claim 12, wherein said mammal is selected from the group consisting of felids and primates.

22. The method of claim 12, wherein said mammal is selected from the group consisting of domestic cats and humans.

23. A method to protect a human from cat scratch disease comprising administering to a domestic cat in contact with said human a therapeutic composition comprising:
   (a) an isolated *B. henselae* antigen comprising whole inactivated *B. henselae* cells; and
   (b) an adjuvant comprising PCPP.

24. The method of claim 23, wherein said *B. henselae* cells are grown on agar.

25. The method of claim 23, wherein said *B. henselae* cells are grown on eukaryotic cells, said cells being selected from the group consisting of Vero cells, cat cells, mouse cells, and human cells.

26. The method of claim 23, wherein said *B. henselae* cells are grown in broth suspension culture.

27. The method of claim 23, wherein said cells are inactivated by a method selected from the group consisting of formalin inactivation, gamma-irradiation, heat inactivation, beta-propiolactone inactivation, UV irradiation, psorilen inactivation, and BEI inactivation.

28. The method of claim 23, wherein said PCPP is a microparticle.

29. The method of claim 23, wherein said PCPP is a microparticle having said isolated *B. henselae* antigen microencapsulated therein.

30. The method of claim 23, wherein said composition further comprises a component selected from the group consisting of an excipient, a carrier, and an additional adjuvant.

31. The method of claim 23, wherein said therapeutic composition comprises:
   (a) a *B. henselae* antigen selected from the group consisting of iBhV-Ag, iBhA-Ag, and iBhB-Ag; and
   (b) an adjuvant comprising PCPP.

32. The method of claim 23, wherein said mammal is selected from the group consisting of felids and primates.

33. The method of claim 23, wherein said mammal is selected from the group consisting of domestic cats and humans.

34. A method to produce a therapeutic composition to protect a mammal from *B. henselae* infection comprising the steps of:
   (a) growing *B. henselae* cells;
   (b) preparing an isolated *B. henselae* antigen comprising whole inactivated *B. henselae* cells from said cells; and
   (c) mixing said isolated *B. henselae* antigen with an adjuvant comprising PCPP.

35. The method of claim 34, wherein said step of growing is selected from the group consisting of growing said *B. henselae* cells on eukaryotic cells, growing said *B. henselae* cells on agar, and growing said *B. henselae* cells in broth suspension culture.

36. The method of claim 34, wherein said step of mixing is selected from the group consisting of combining said isolated *B. henselae* antigen with soluble PCPP, combining said isolated *B. henselae* antigen with a PCPP microparticle, and microencapsulating said isolated *B. henselae* antigen in a PCPP microparticle.

* * * * *

UNITED STATES PATENT AND TRADEMARK OFFICE
CERTIFICATE OF CORRECTION

PATENT NO : 5,958,414
DATED : Sep. 28, 1999
INVENTOR(S): Russell L. Regnery, Jane A. Rooney, Sharon A. Jenkins It is certified that error appears in the above-identified patent and that said Letters Patent is hereby corrected as shown below:

Column 20, line 17, delete "Barionella" and insert therefor
--Bartonella--

Column 20, line 21, delete "carboxylatophenoxv" and insert therefor
--carboxylatophenoxy--

Column 20, line 34, delete "propiolactonc" and insert therefor
--propiolactone--

Signed and Sealed this

Fifteenth Day of August, 2000

Attest:

Q. TODD DICKINSON

Attesting Officer     Director of Patents and Trademarks